United States Patent
Itoi

(10) Patent No.: US 9,000,171 B2
(45) Date of Patent: Apr. 7, 2015

(54) ORGANIC ELECTROLUMINESCENCE MATERIAL INCLUDING A SUBSTITUTED ACRIDINE COMPOUND AND ORGANIC ELECTROLUMINESCENCE DEVICE INCLUDING THE SAME

(71) Applicant: Samsung Display Co., Ltd., Yongin, Gyeonggi-Do (KR)

(72) Inventor: Hiroaki Itoi, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 0 days.

(21) Appl. No.: 14/083,746

(22) Filed: Nov. 19, 2013

(65) Prior Publication Data

US 2014/0142300 A1    May 22, 2014

(30) Foreign Application Priority Data

Nov. 19, 2012 (JP) .................. 2012-253453

(51) Int. Cl.
 *C07D 209/82* (2006.01)
 *C07D 219/02* (2006.01)
 *H01L 51/00* (2006.01)
 *C07C 211/00* (2006.01)
 *H01L 51/50* (2006.01)

(52) U.S. Cl.
 CPC .......... *H01L 51/006* (2013.01); *H01L 51/0061* (2013.01); *C07C 211/00* (2013.01); *H01L 51/0072* (2013.01); *H01L 51/0081* (2013.01); *H01L 51/5056* (2013.01)

(58) Field of Classification Search
 CPC .......................... C07D 209/82; C07D 219/02
 USPC .......................................... 546/102; 548/427
 See application file for complete search history.

(56) References Cited

U.S. PATENT DOCUMENTS

2011/0240968 A1  10/2011  Kim et al.

FOREIGN PATENT DOCUMENTS

| EP | 2182040 A2 | 5/2010 |
|---|---|---|
| JP | 2000-021572 A | 1/2000 |
| JP | 2004-307384 A | 11/2004 |
| JP | 2005-516059 A | 6/2005 |
| JP | 2010-241801 A | 10/2010 |
| JP | 2011-231025 A | 11/2011 |
| JP | 2012-507507 A | 3/2012 |
| KR | 10-2011-0066763 A | 6/2011 |
| KR | 10-2012-0084238 A | 7/2012 |
| WO | WO-2011/019156 A1 | 2/2011 |
| WO | WO 2011/088877 A1 | 7/2011 |
| WO | WO 2011/107186 A2 | 9/2011 |
| WO | WO-2012/008281 A1 | 1/2012 |
| WO | WO 2012/049828 A1 | 4/2012 |
| WO | WO 2012/090806 A1 | 7/2012 |

OTHER PUBLICATIONS

Sivaraman Balasubramaniam, et al., "Weinreb Amide Based New Synthetic Equivalents for Convenient Access to Immunosuppresive Agent FTY720 and Analogues", SYNLETT 2007, No. 18, pp. 2841-2846.

*Primary Examiner* — Douglas M Willis
(74) *Attorney, Agent, or Firm* — Lee & Morse, P.C.

(57) ABSTRACT

An organic electroluminescence (EL) material and an organic EL device, the organic EL material being represented by Formula 1, below:

[Formula 1]

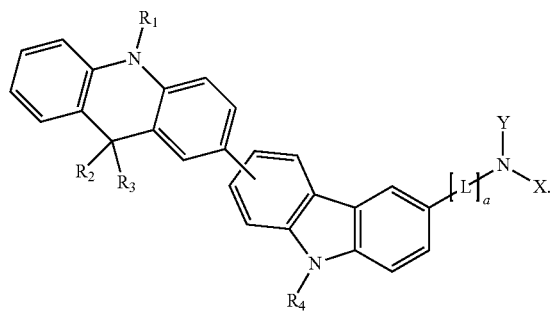

5 Claims, 1 Drawing Sheet

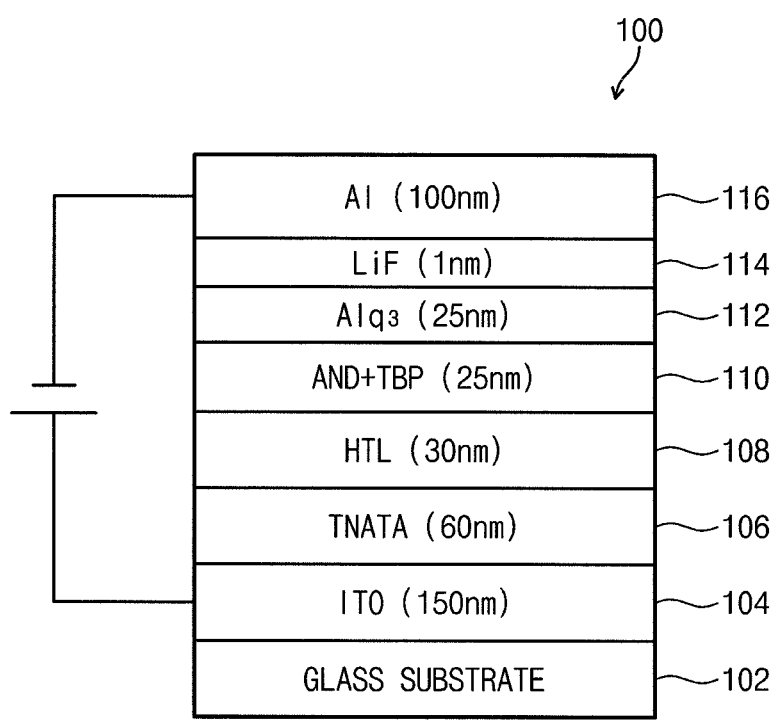

ORGANIC ELECTROLUMINESCENCE MATERIAL INCLUDING A SUBSTITUTED ACRIDINE COMPOUND AND ORGANIC ELECTROLUMINESCENCE DEVICE INCLUDING THE SAME

CROSS-REFERENCE TO RELATED APPLICATION

Japanese Patent Application No. 2012-253453, filed on Nov. 19, 2012, in the Japanese Intellectual Property Office, and entitled: "Organic Electroluminescence Material Comprising Amine Derivative and Organic Electroluminescence Device Using The Same," is incorporated by reference herein in its entirety.

BACKGROUND

1. Field

Embodiments relate to an organic EL material and an organic EL device including the same.

2. Description of the Related Art

In recent years, organic electroluminescence (EL) displays that are one type of image displays have been actively developed. Unlike a liquid crystal display and the like, the organic EL display may be a so-called self-luminescent display in which holes and electrons injected from an anode and a cathode are recombined in a light-emitting layer to thus emit a light from a light-emitting material including an organic compound of the light-emitting layer, thereby displaying an image.

An example of a light-emitting device may include an organic EL device that includes an anode, a hole transport layer on the anode, a light-emitting layer on the hole transport layer, an electron transport layer on the light-emitting layer, and a cathode on the electron transport layer. Holes injected from the anode may be transported into the light-emitting layer via the hole transport layer. Electrons may be injected from the cathode, and then transported into the light-emitting layer via the electron transport layer.

SUMMARY

Embodiments are directed to an organic EL material and an organic EL device including the same.

The embodiments may be realized by providing an organic electroluminescence (EL) material represented by Formula 1, below:

[Formula 1]

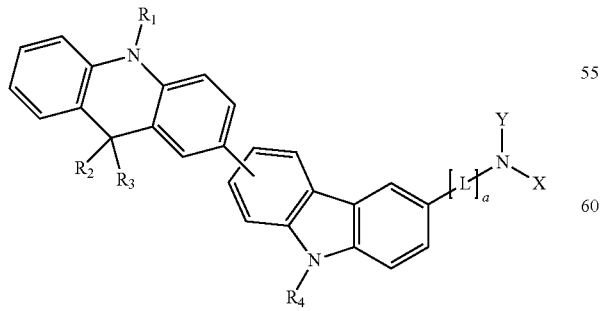

wherein X and Y are each independently an aryl group or a heteroaryl group having 6 to 18 carbon atoms, L is an arylene group or a heteroarylene group having 6 to 18 carbon atoms, $R_1$ to $R_4$ are each independently a hydrogen atom, a halogen atom, an aryl group or heteroaryl group having 6 to 18 carbon atoms, or an alkyl group having 1 to 12 carbon atoms, and a is an integer satisfying $0 \leq a \leq 3$.

X may be a monovalent group represented by one of groups (2) to (10), below:

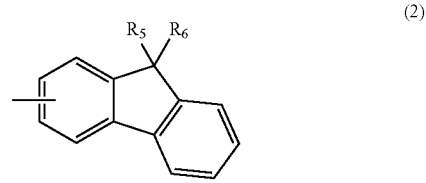
(2)

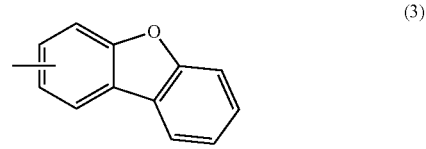
(3)

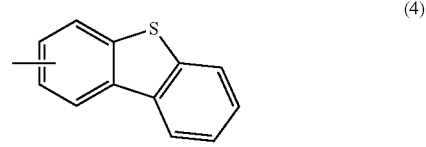
(4)

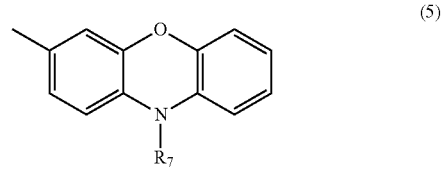
(5)

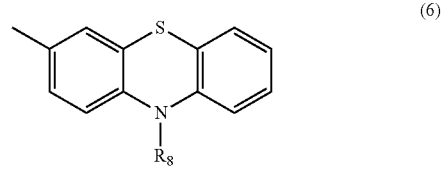
(6)

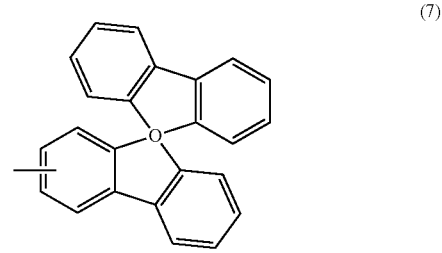
(7)

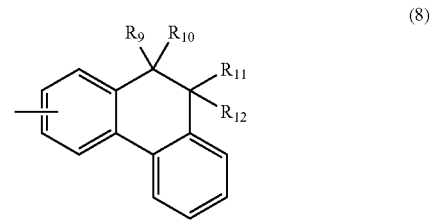
(8)

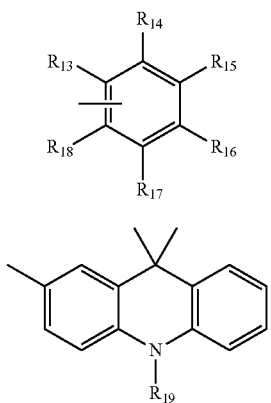

wherein $R_5$ to $R_{17}$ and $R_{19}$ are each independently a hydrogen atom, a halogen atom, an aryl group or hetero aryl group having 6 to 18 carbon atoms, or an alkyl group having 1 to 12 carbon atoms.

The embodiments may also be realized by providing an organic electroluminescence (EL) device including an organic EL material represented by Formula 1, below:

[Formula 1]

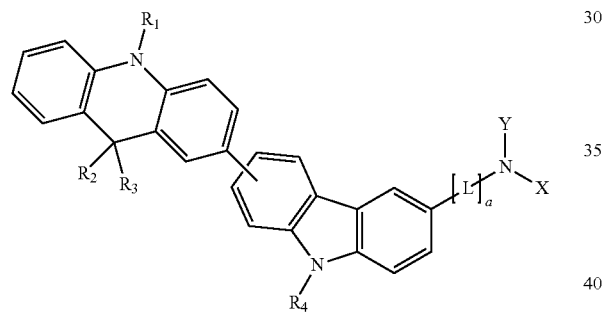

wherein X and Y are each independently an aryl group or a heteroaryl group having 6 to 18 carbon atoms, L is an arylene group or a heteroarylene group having 6 to 18 carbon atoms, $R_1$ to $R_4$ are each independently a hydrogen atom, a halogen atom, an aryl group or heteroaryl group having 6 to 18 carbon atoms, or an alkyl group having 1 to 12 carbon atoms, and a is an integer satisfying $0 \leq a \leq 3$.

X may be a monovalent group represented by one of groups (2) to (10), below:

(2)

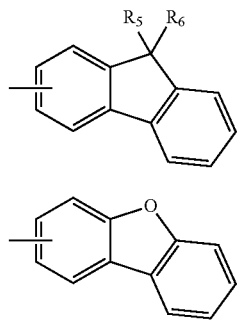

(3)

(4)
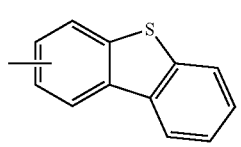

(5)
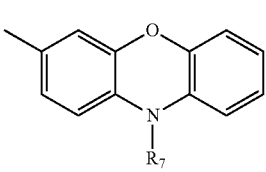

(6)
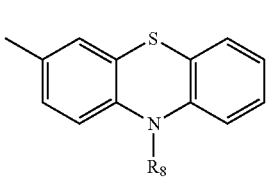

(7)
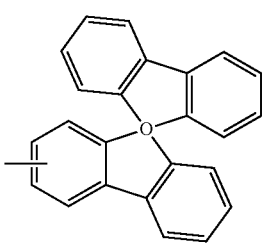

(8)
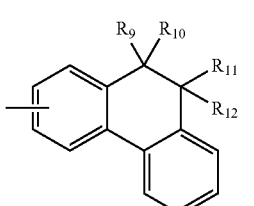

(9)
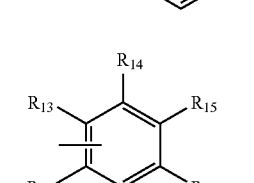

(10)
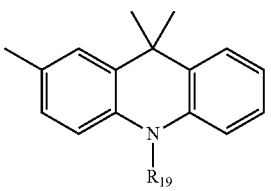

wherein $R_5$ to $R_{17}$ and $R_{19}$ are each independently a hydrogen atom, a halogen atom, an aryl group or hetero aryl group having 6 to 18 carbon atoms, or an alkyl group having 1 to 12 carbon atoms.

The embodiments may also be realized by providing an organic electroluminescence(EL) material represented one of compounds 1 to 24, below:

1
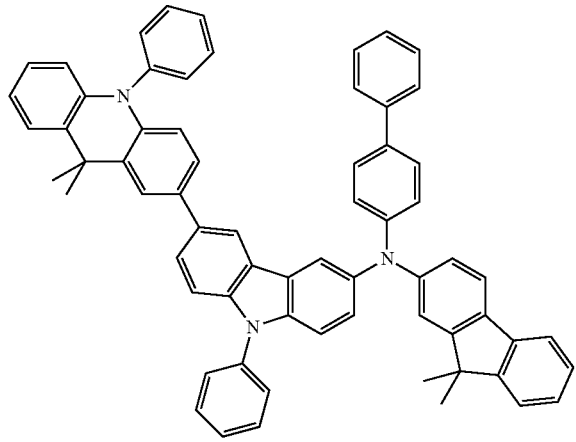
2
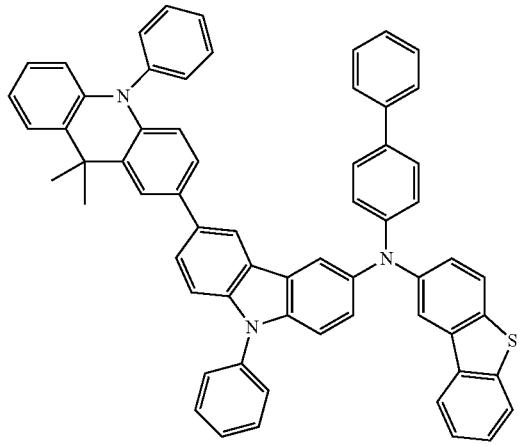
3
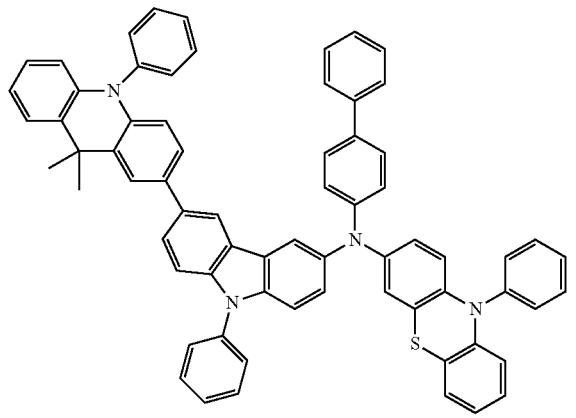
4
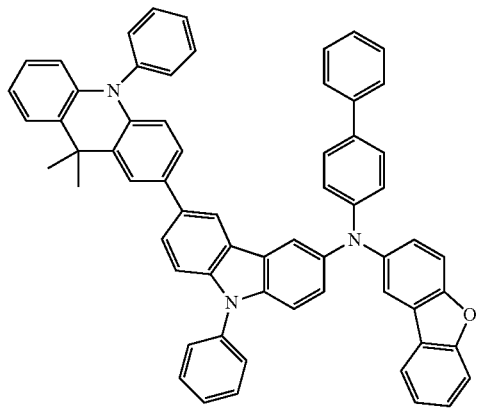
5
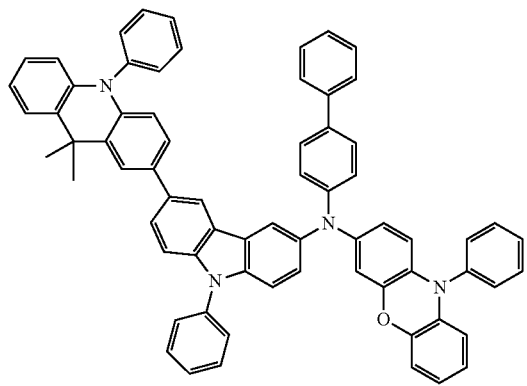
6
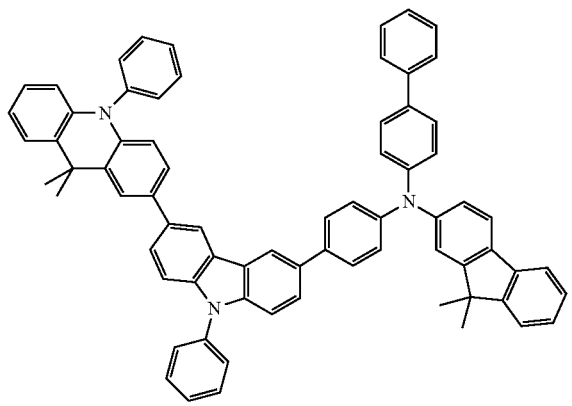

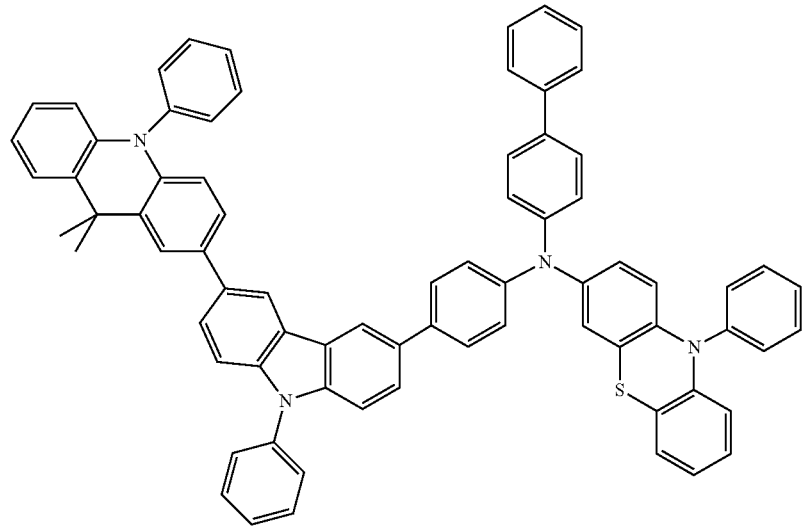
7
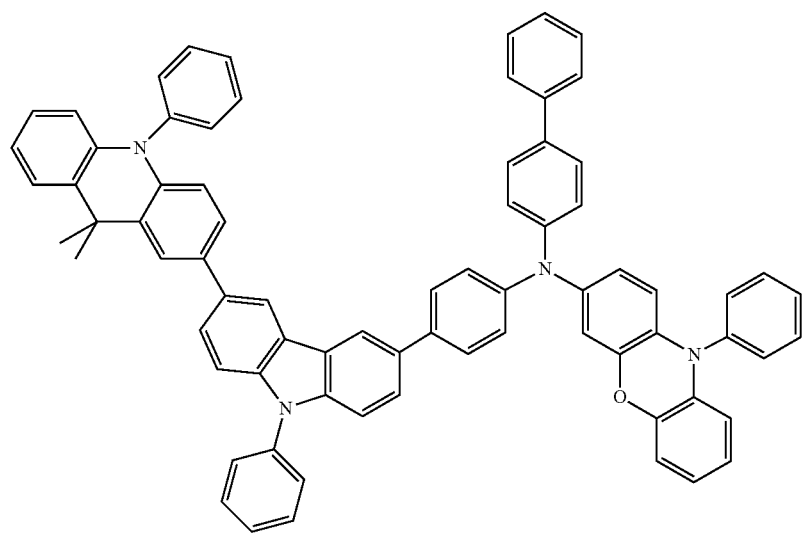
8
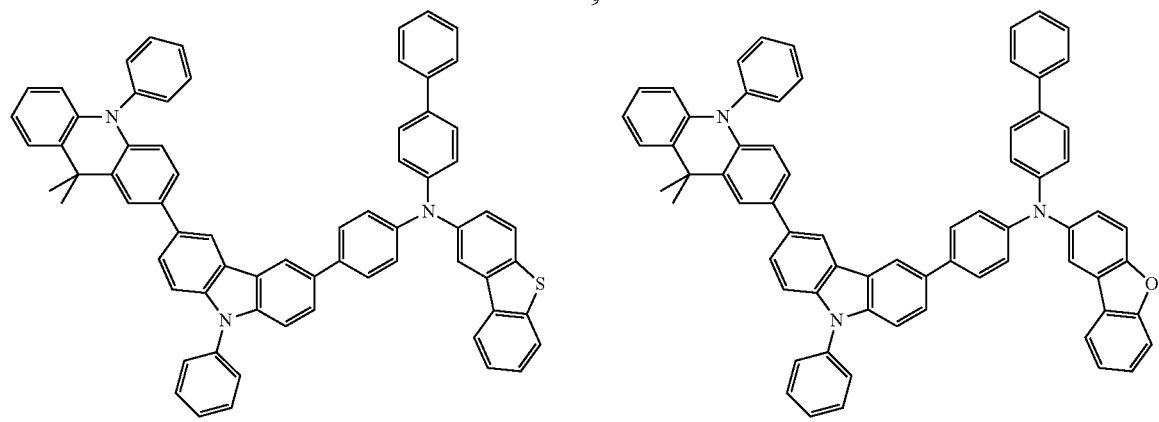

-continued
11
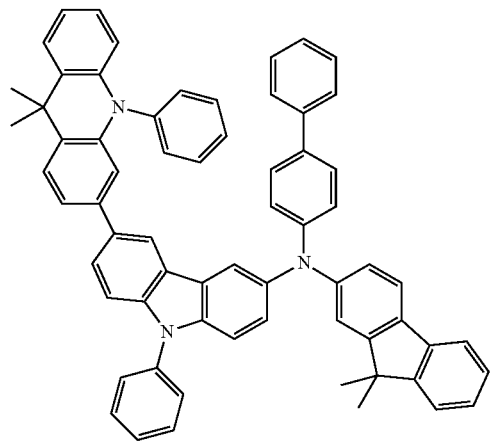
12
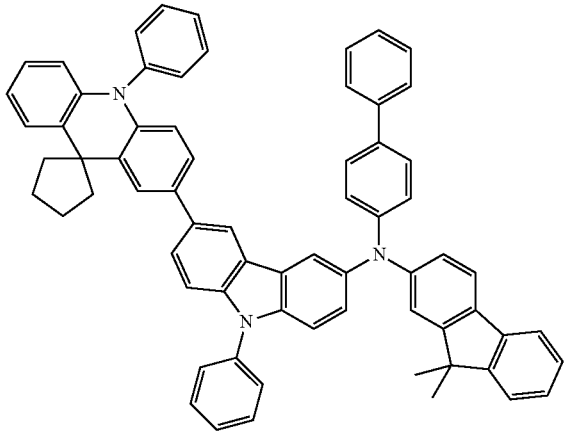
13
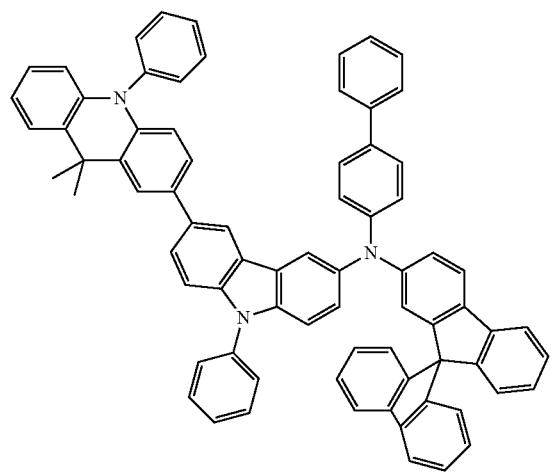
14
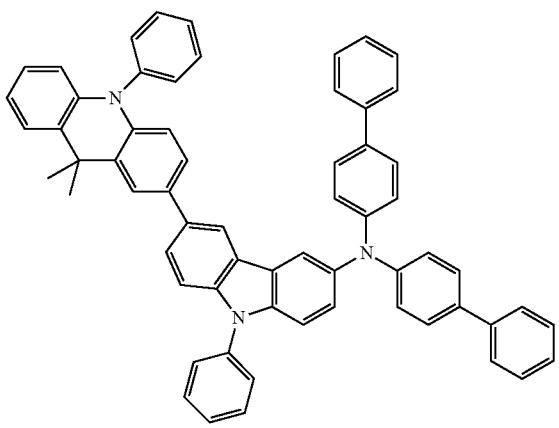
15
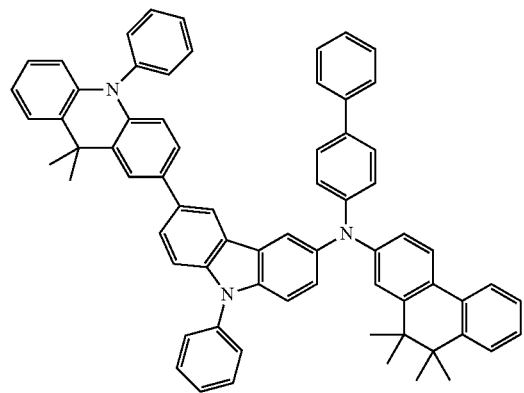
16
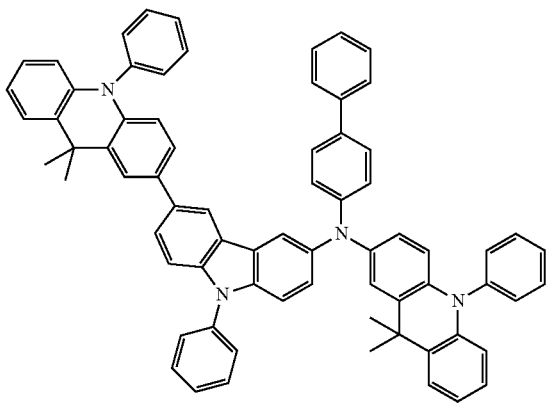

17
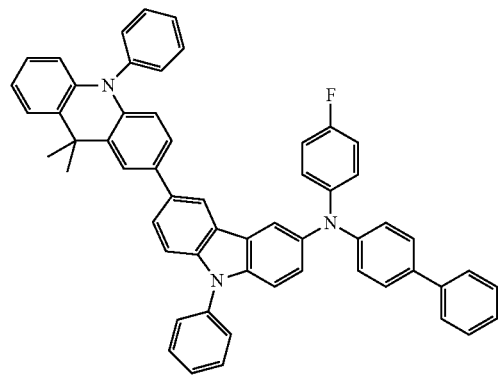
18
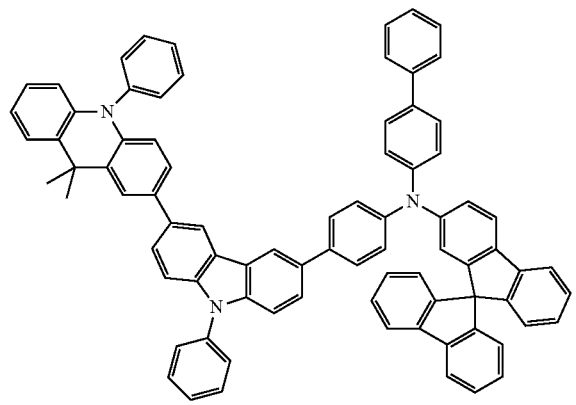
19
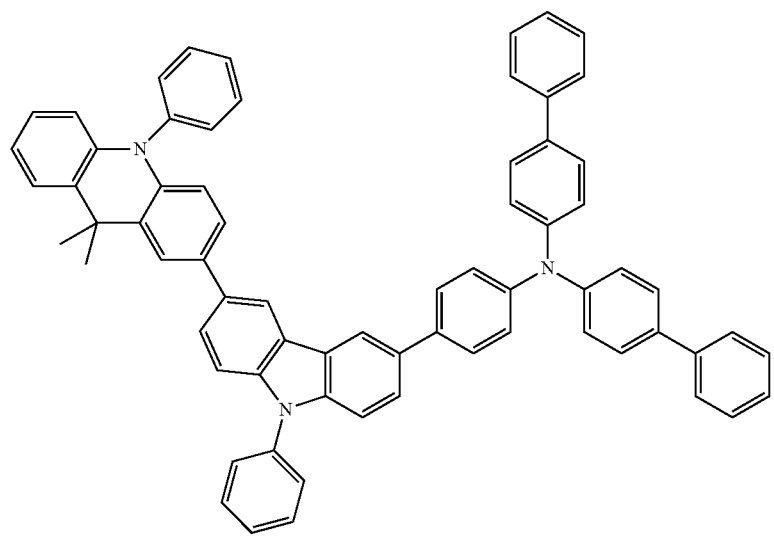
20
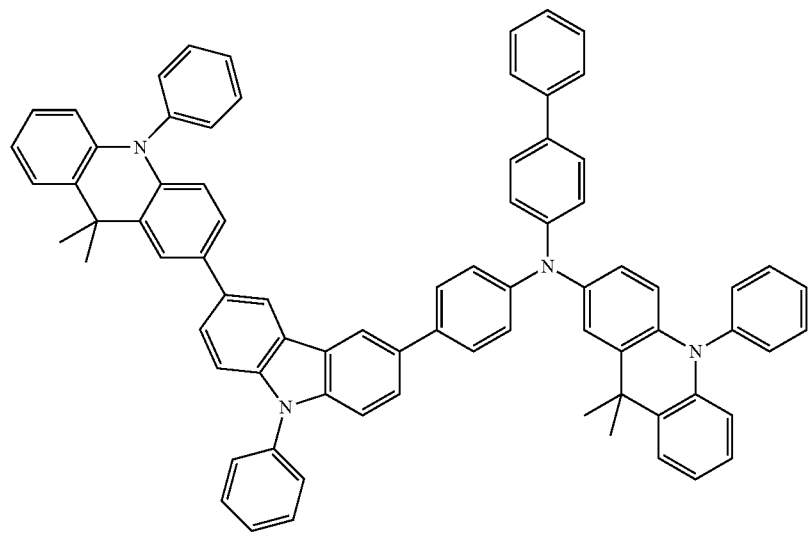

-continued
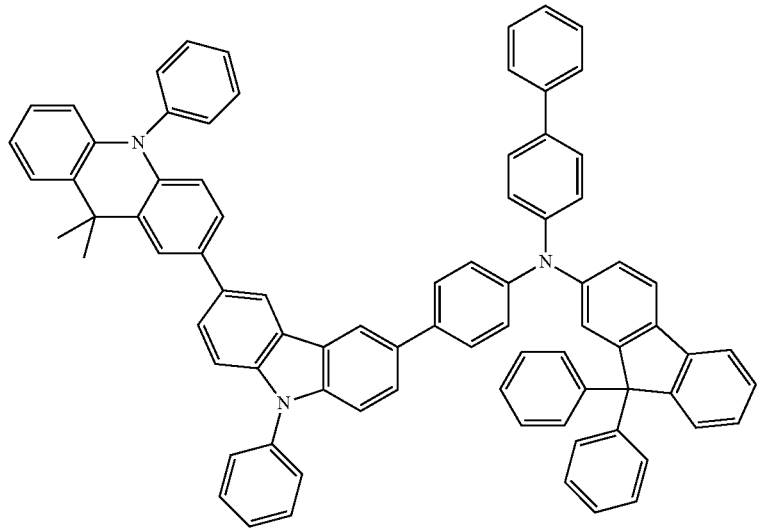
21
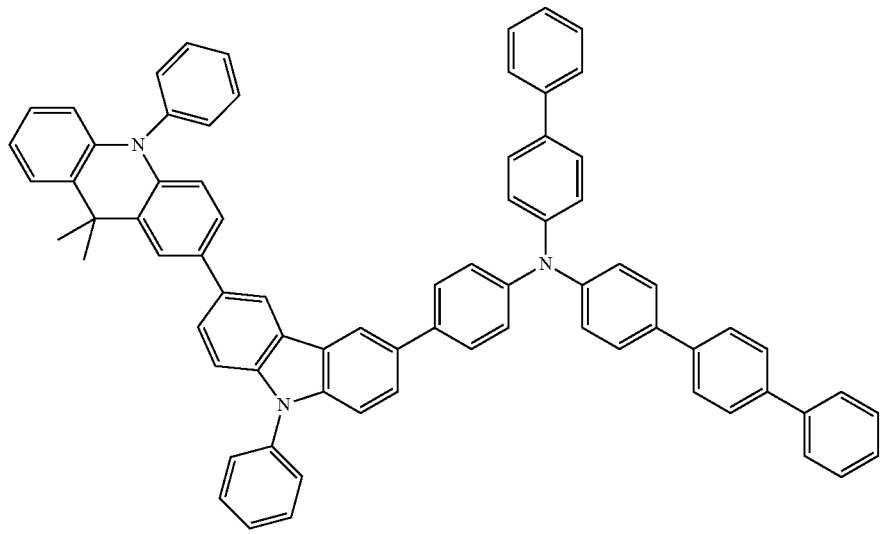
22
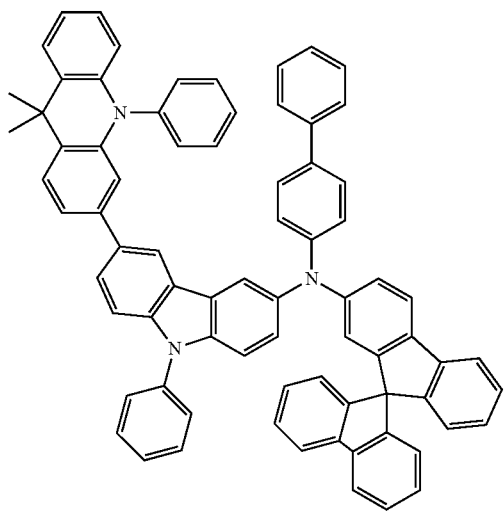
23
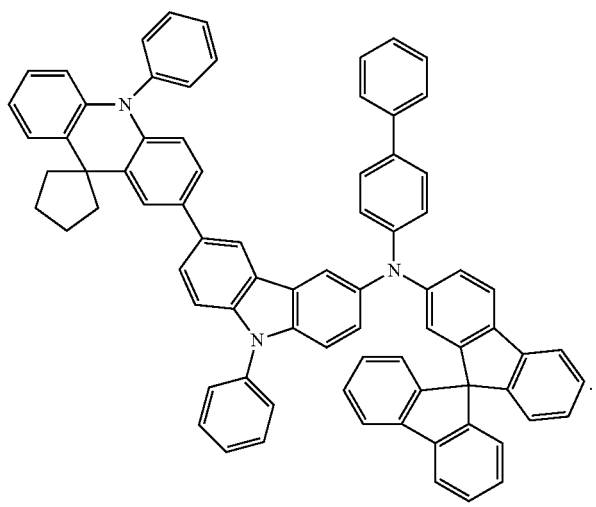
24

BRIEF DESCRIPTION OF THE DRAWING

Features will be apparent to those of skill in the art by describing in detail exemplary embodiments with reference to the attached drawing in which:

FIG. 1 illustrates a schematic view of an organic EL device.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figure, the dimensions of layers and regions may be exaggerated for clarity of illustration. Like reference numerals refer to like elements throughout.

Luminous efficiency of an organic electroluminescence (EL) device may be improved by using a particular compound, e.g., an amine derivative having an acridine group and a carbazole group, as a hole transport material of the organic EL device. Hereinafter, an amine derivative having an acridine group and a carbazole group will be described.

In an implementation, the amine derivative having an acridine group and a carbazole group that may be used as a hole transport material of a hole transport layer of an organic EL device may be a compound represented by Formula 1, below.

[Formula 1]

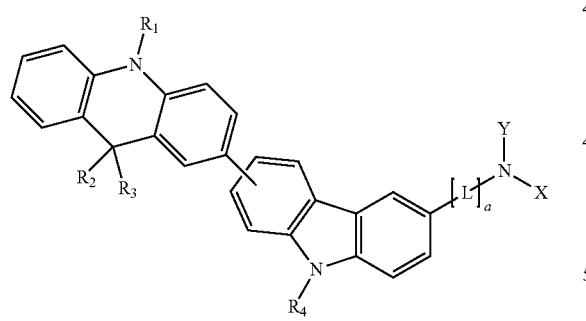

In Formula 1, X and Y may each independently be an aryl group or a heteroaryl group (e.g., having 6 to 18 carbon atoms). L may be an arylene group or a heteroarylene group having 6 to 18 carbon atoms. $R_1$ to $R_4$ may each independently be a hydrogen atom, a halogen atom, an aryl or heteroaryl group, e.g., having 6 to 18 carbon atoms, or an alkyl group having 1 to 12 carbon atoms. In an implementation, $R_2$ and/or $R_3$ may be or may include a cyclic group or a Spiro structure. a may be an integer satisfying 0≤a≤3, e.g., may be 0, 1, 2, or 3.

In an implementation, X may be a monovalent group represented by one of groups (2) to (10), below.

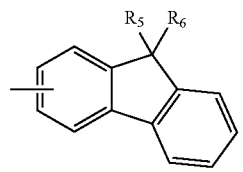
(2)

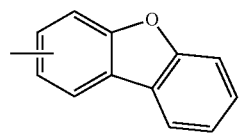
(3)

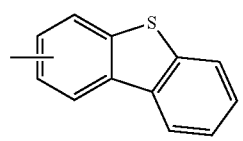
(4)

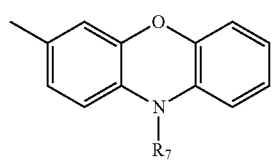
(5)

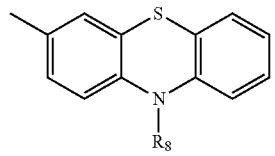
(6)

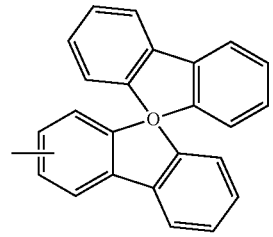
(7)

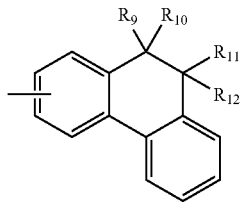
(8)

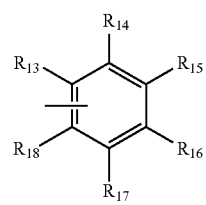
(9)

-continued (10)

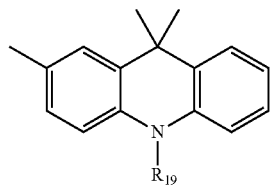

In groups (2) to (10), $R_5$ to $R_{17}$ and $R_{19}$ may each independently be a hydrogen atom, a halogen atom, an aryl or heteroaryl group (e.g., having 6 to 18 carbon atoms), or an alkyl group having 1 to 12 carbon atoms.

In an implementation, in Formula 1, Y may be, e.g., a phenyl group, a biphenyl group, or a terphenyl group. In an implementation, Y may be a biphenyl group.

In an implementation, X and Y may each independently be a hydrogen atom, a halogen atom, an aryl or heteroaryl group (e.g., having 6 to 18 carbon atoms), or an alkyl group having 1 to 12 carbon atoms. L may be an arylene group or heteroarylene group having 6 to 18 carbon atoms. In an implementation, $R_1$ to $R_{17}$ and $R_{19}$ may each independently be a phenyl group, a biphenyl group, a methyl group, a hydrogen atom, or a fluorine atom. In an implementation, L may be a phenylene group or a biphenylene group. In an implementation, L may be a phenylene group. In an implementation, "a" may be an integer satisfying 0≤a≤3.

In the amine derivative having an acridine group and a carbazole group according to an embodiment, charge stability of the hole transport material may be improved by the carbazole group. In addition, undesirable crystallization of the hole transport material during an operation of the organic EL device may be suppressed due to the presence of a substituent acridine group. Thus, high efficiency of the organic EL device may be achieved. For example, in a region of emitting a blue light, a high luminous efficiency may be achieved.

In the amine derivative having an acridine group and a carbazole group according to an embodiment, dimethyl fluorene, dibenzofuran, dibenzothiophene, phenothiazine, phenoxazine (e.g., examples of monovalent groups represented by X of Formula 1), or the like, may be an electron-rich substituent group. Thus, hole transportability may be improved. Also, in the amine derivative having an acridine group and a carbazole group, a change in electron distribution of HOMO (Highest Occupied Molecular Orbital) may occur by including L, e.g., by introducing an arylene group or heteroarylene group (e.g., a phenylene group or the like), between the amine and the carbazole group. Therefore, by introducing an arylene group or heteroarylene group (e.g., a phenylene group) between the amine and the carbazole group, a band gap may be controlled, and the hole transportability may be improved.

Examples of the amine derivatives having an acridine group and a carbazole group according to an embodiment may include compounds 1-24, below.

1

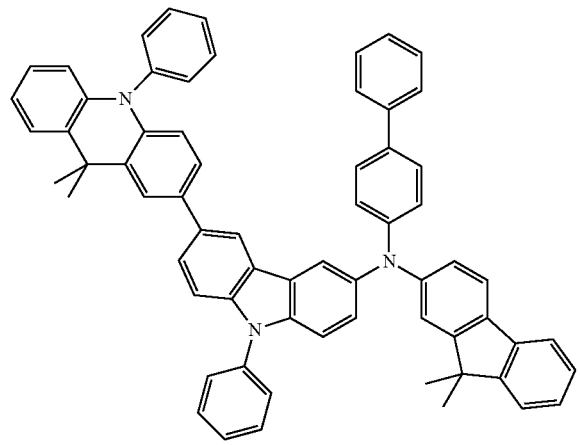

2

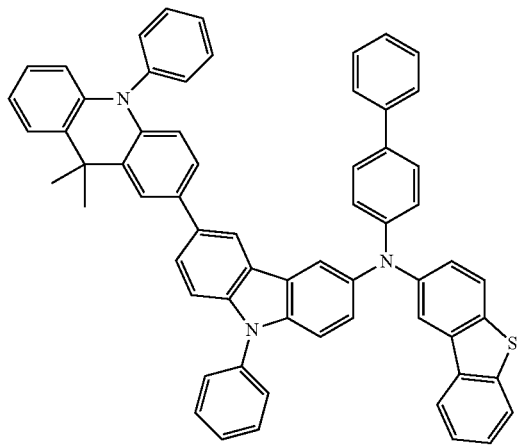

3

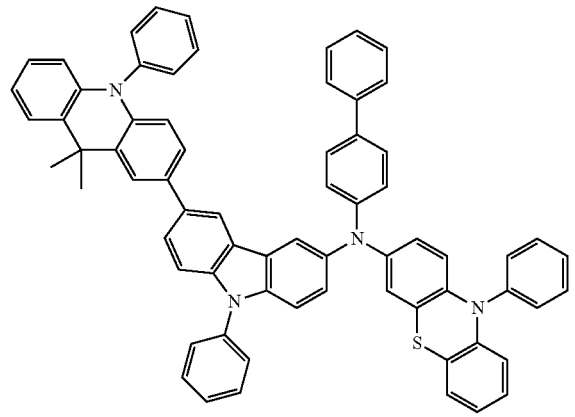

4

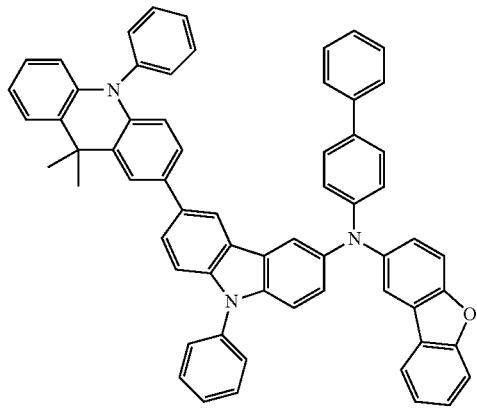

5
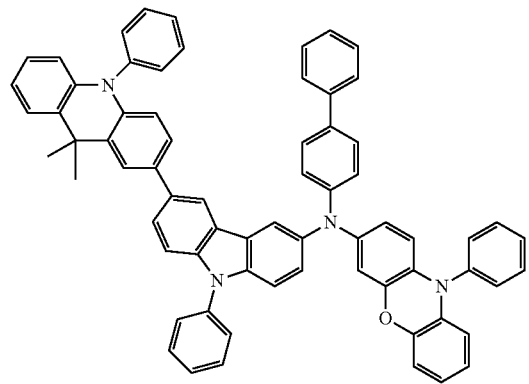
6
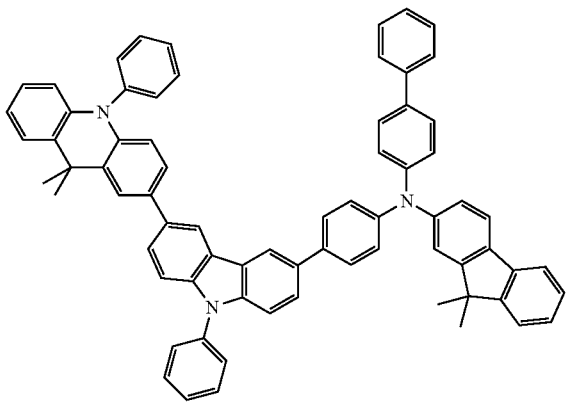
7
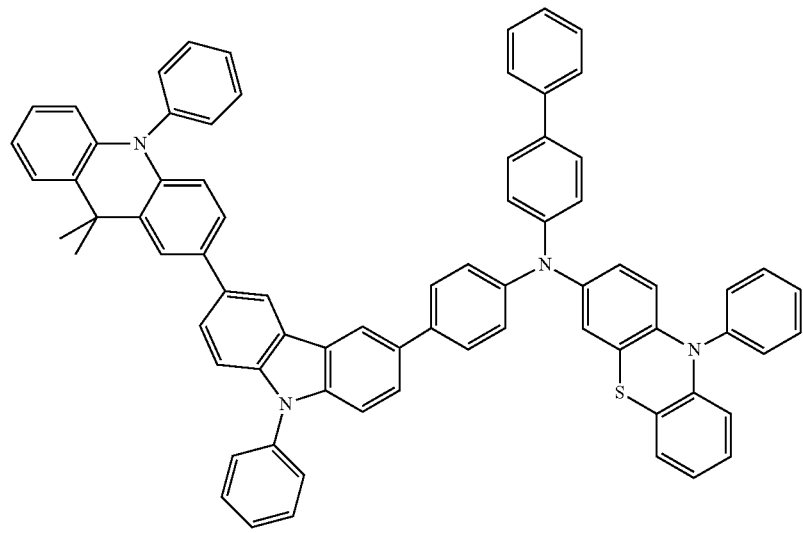
8
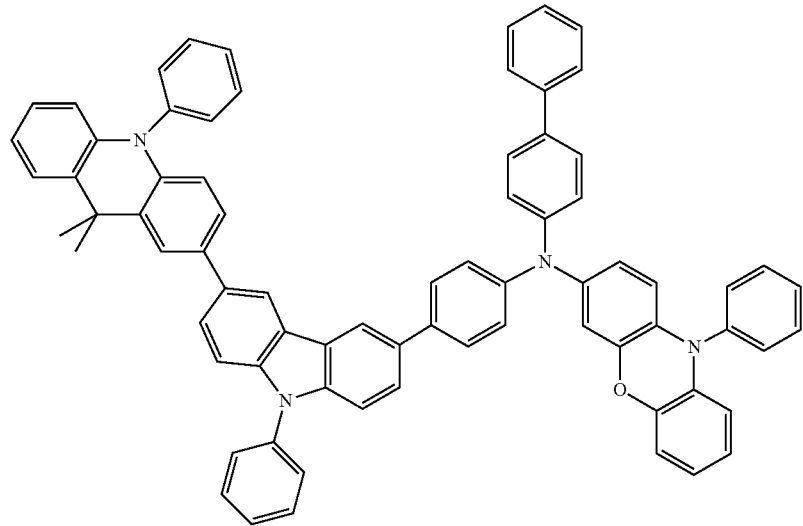

9
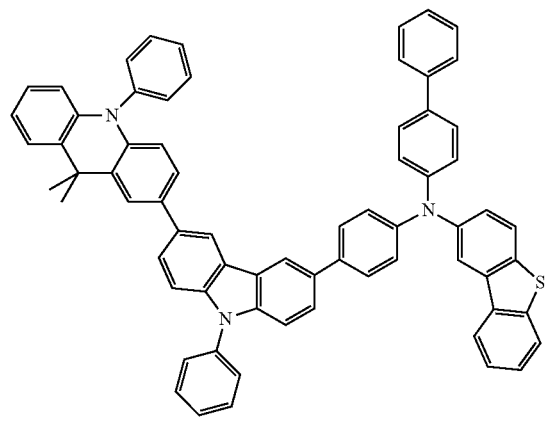
10
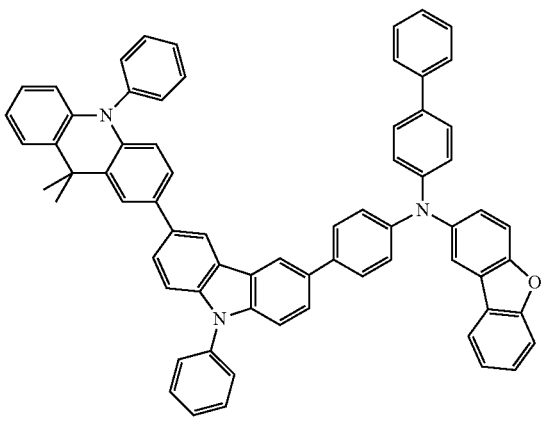
11
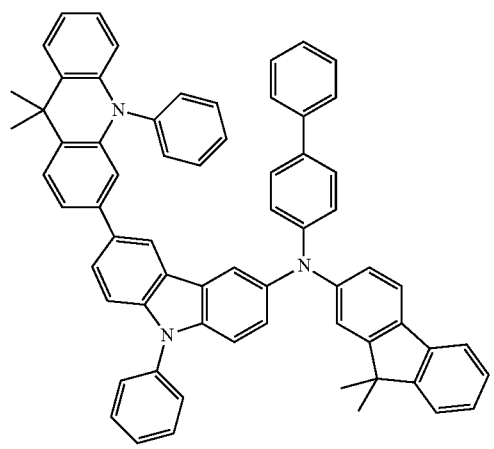
12
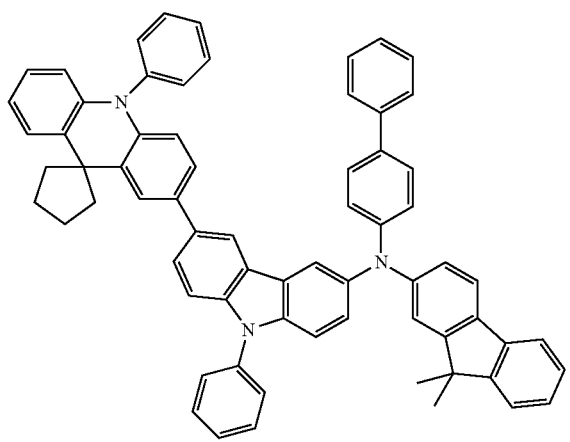
13
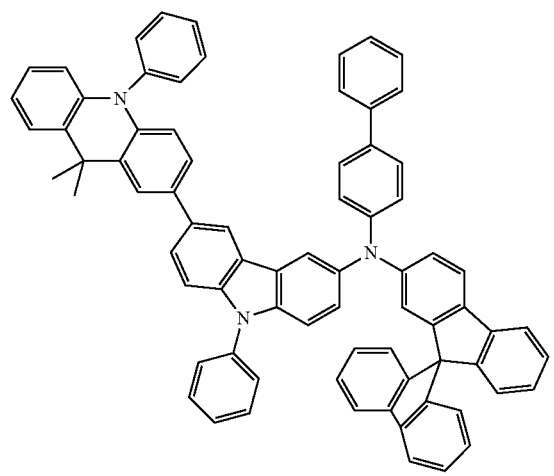
14
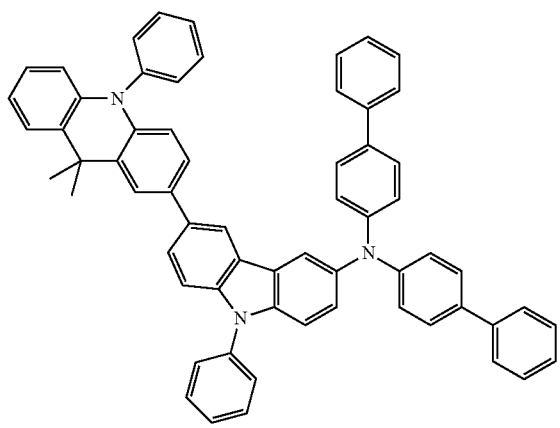

15
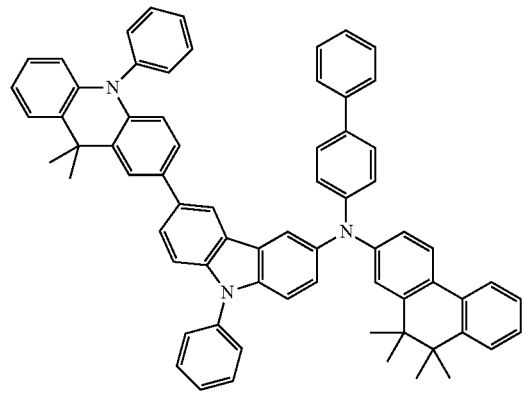
16
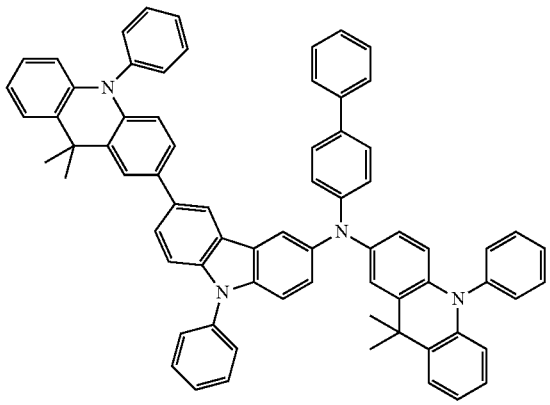
17
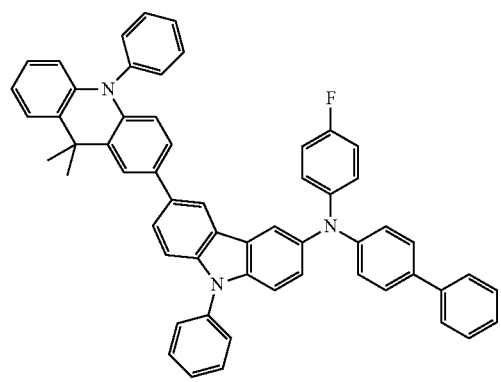
18
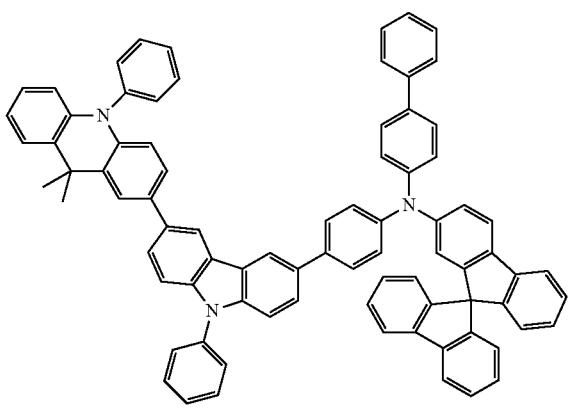
19
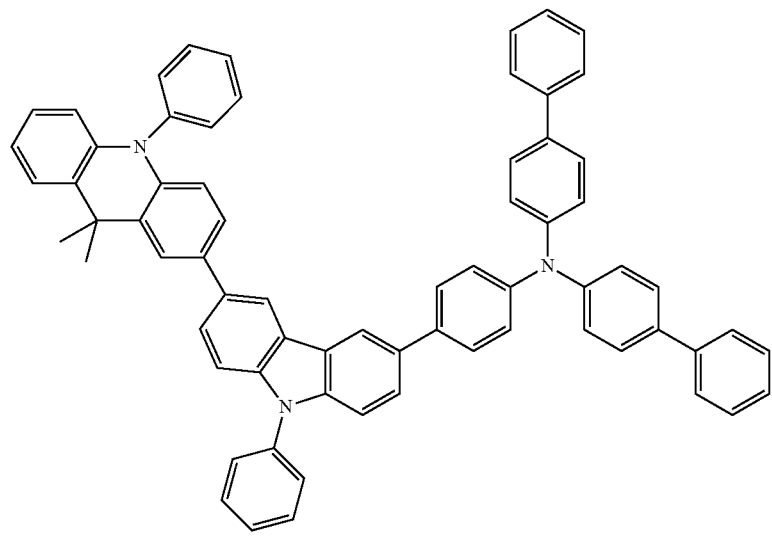

20
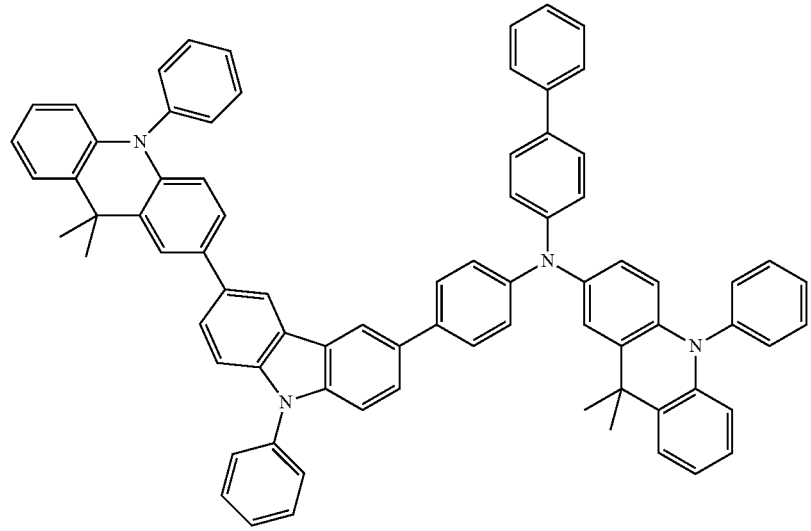
21
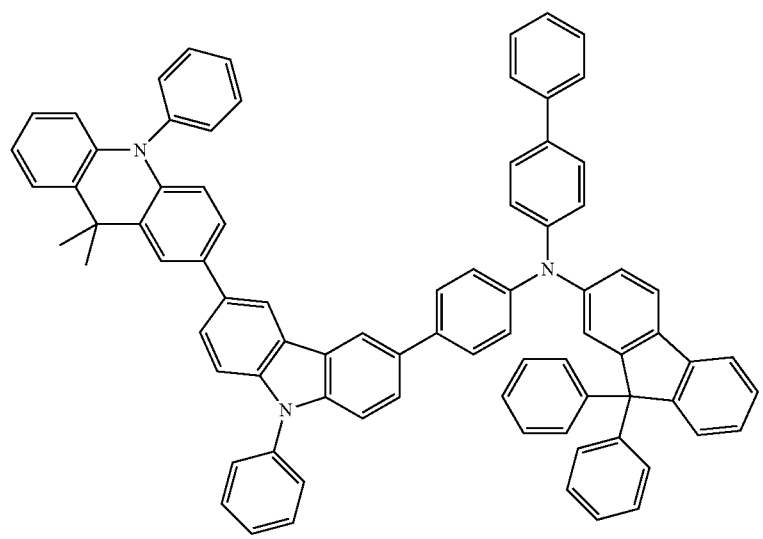
22
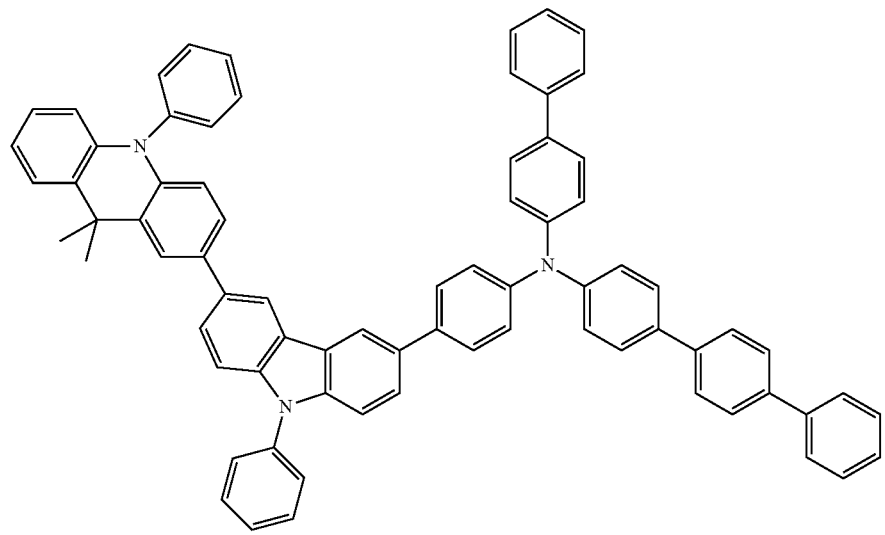

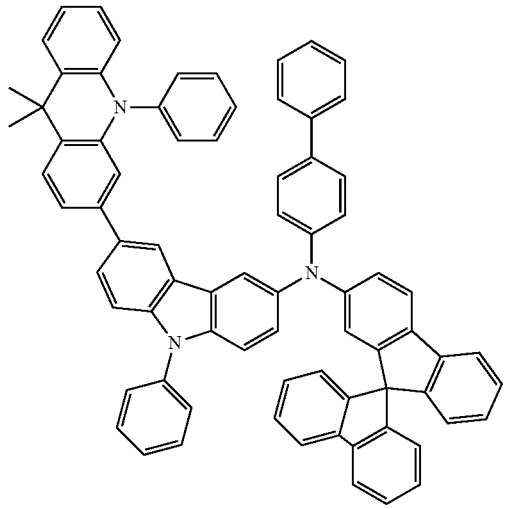

23

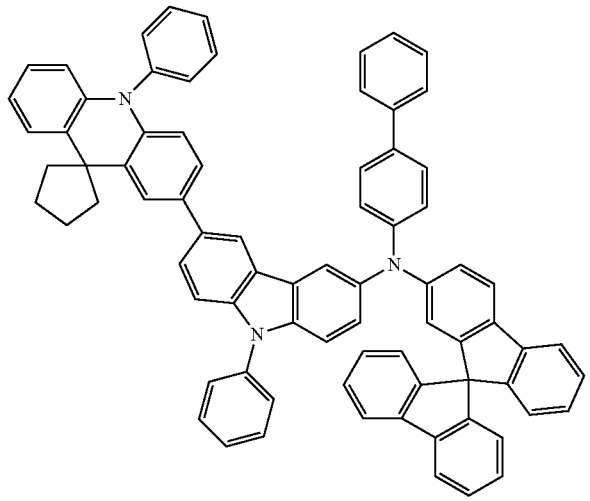

24

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples An example of a method of synthesizing a compound for an amine derivative having an acridine group and a carbazole group according to an embodiment will now be described with reference to Reaction Scheme 1, below.

[Reaction Scheme 1]

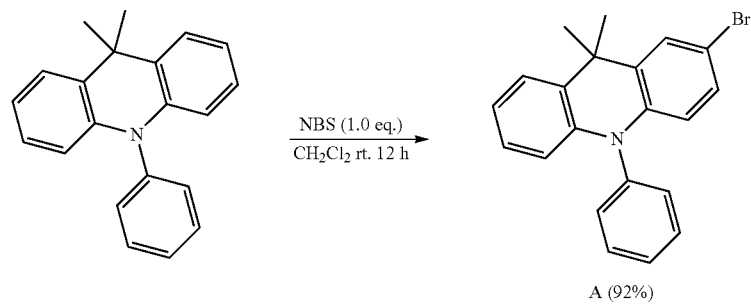

A (92%)

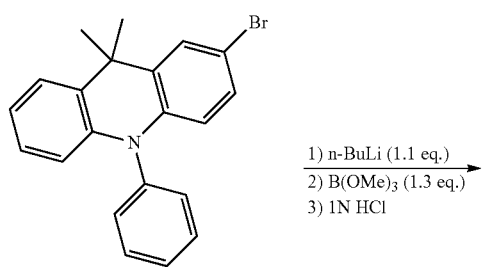

-continued
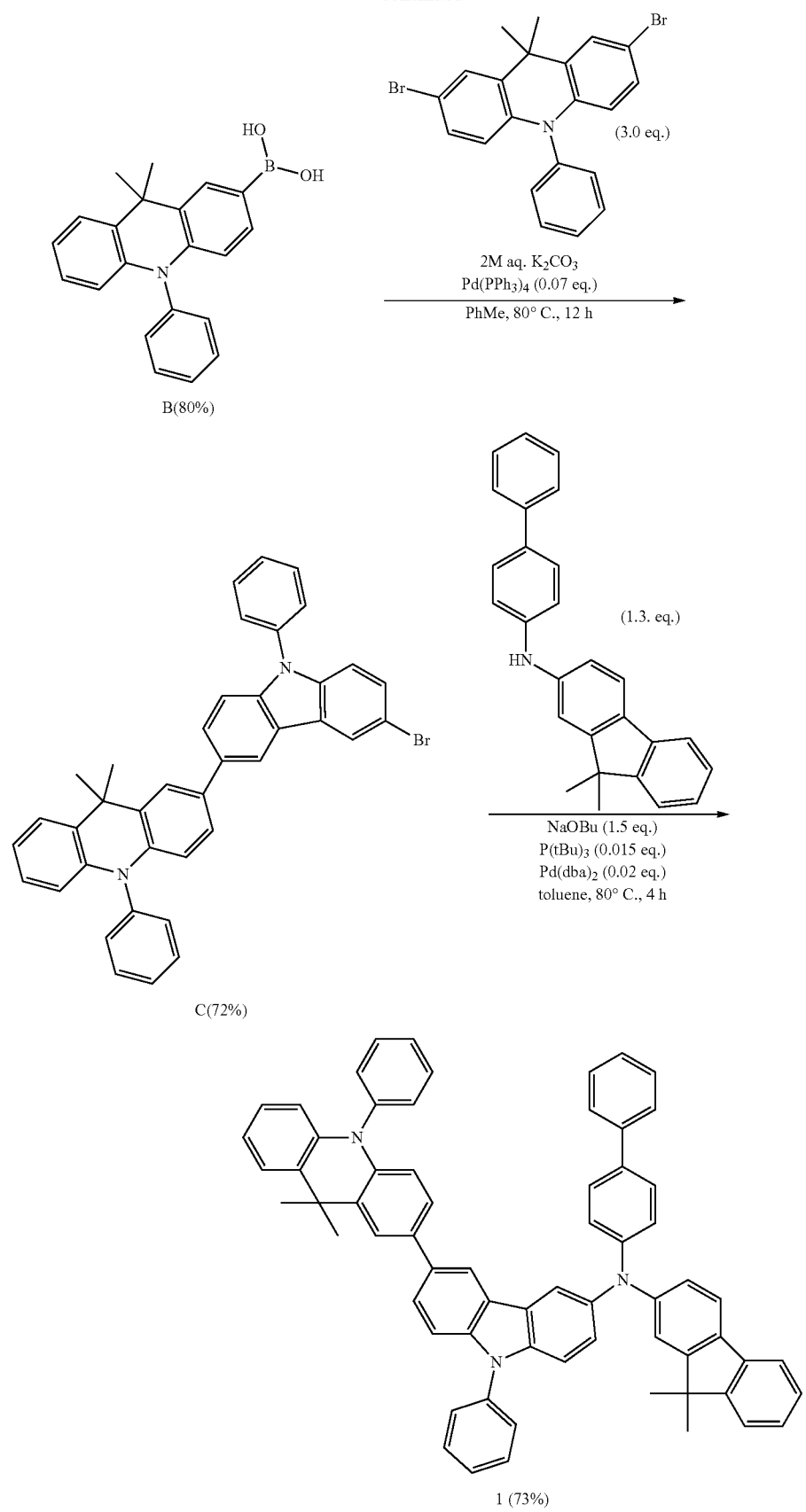

Synthesis of Compound A 14.2 g (1.0 equivalent) of N-bromosuccinic acid imide was added to a 300 mL three-necked flask containing 23.0 g of 9,9-dimethyl-10-phenylacridine under an argon atmosphere and stirred for 12 hours at room temperature in 200 mL of dichloromethane ($CH_2Cl_2$). Water was added to a reaction solution to separate an organic layer, and a solvent was removed by distillation.

The remaining mixture was purified by silica gel column chromatography (in a mixed solvent of chloroform and hexane), and was recrystallized in a mixed solvent of toluene and hexane to obtain 29.4 g of white solid compound A (yield: 92%). FAB-MS measurement was performed and compound A was identified from the detected molecular weight of 365.363.

Synthesis of Compound B 150 mL of anhydrous tetrahydrofuran (THF, −78° C.) and 200 g of compound A were introduced into a 300 mL three-necked flask under an argon atmosphere. 37.7 mL (1.1 equivalents) of 1.6 M n-butyllithium/n-hexane solution (n-BuLi) was dropped in the mixture, and the mixture was stirred for 1 hour. Then, 7.80 mL (1.3 equivalents) of trimethoxyborane ($B(OMe)_3$) was added thereto, and stirred for 2 hours to increase the temperature in the reaction system to room temperature. 200 mL of 1N hydrochloric acid was added to the reaction solution, and the mixture was stirred for 3 hours. An organic layer was separated, and the solvent was removed by distillation. A hexane was added to the obtained crude product to separate a precipitated product and obtain 14.5 g of a white solid compound B (yield: 80%). FAB-MS measurement was performed and compound B was identified from the detected molecular weight of 329.

Synthesis of Compound C 4.02 g (3.0 equivalents) of 3,6-dibromo-9-phenylcarbazole, 8 mL of a 2M potassium carbonate aqueous solution, and 0.27 g (0.07 equivalents) of tetrakis(triphenylphosphine) palladium ($Pd(PPh_3)_4$) were added in a 50 mL two-necked flask containing 1.10 g of compound B under argon atmosphere. The mixture was stirred at 80° C. for 12 hours in 35 mL of a toluene solvent. The mixture was cooled in the air, an organic layer was separated, the remaining mixture was purified by silica gel column chromatography (using a mixed solvent of chloroform and hexane), and was recrystallized in a mixed solvent of toluene and hexane to obtain 1.46 g of a white solid compound C (yield: 72%). FAB-MS measurement was performed and compound C was identified from the detected molecular weight of 606.604.

Synthesis of Compound 1

0.80 g of compound C, 0.62 g (1.3 equivalents) of 9,9-dimethyl-N-(4-phenylphenyl)fluoren-2-amine, 0.19 g (1.5 equivalents) of sodium-tert-butoxide, 0.04 g (0.015 equivalents) of tri-tert-butylphosphine, and 0.015 g (0.02 equivalents) of bis(dibenzylideneacetone)palladium were introduced into a two-necked flask containing 300 mL of a dehydrated toluene solvent under argon atmosphere, and the mixture was stirred at 80° C. for 4 hours. The mixture was cooled in the air, water was added to separate an organic layer, the remaining mixture was purified by silica gel column chromatography (using a mixed solvent of chloroform and hexane), and was recrystallized in a mixed solvent of dichloromethane and ethanol to obtain 1.17 g of a white solid compound 1 (yield: 73%). FAB-MS measurement was performed and Compound 1 was identified from the detected molecular weight of 886.

EXAMPLES

Luminous efficiency of an organic EL device (including an amine derivative having an acridine group and a carbazole group as a material for the hole transport layer) according to an embodiment was measured. The above-described Compound 1 was used as a hole transport material for a hole transport layer of the organic EL device. For comparison, Comparative compounds 1, 2, and 3 were used as materials for hole transport layers of organic EL devices.

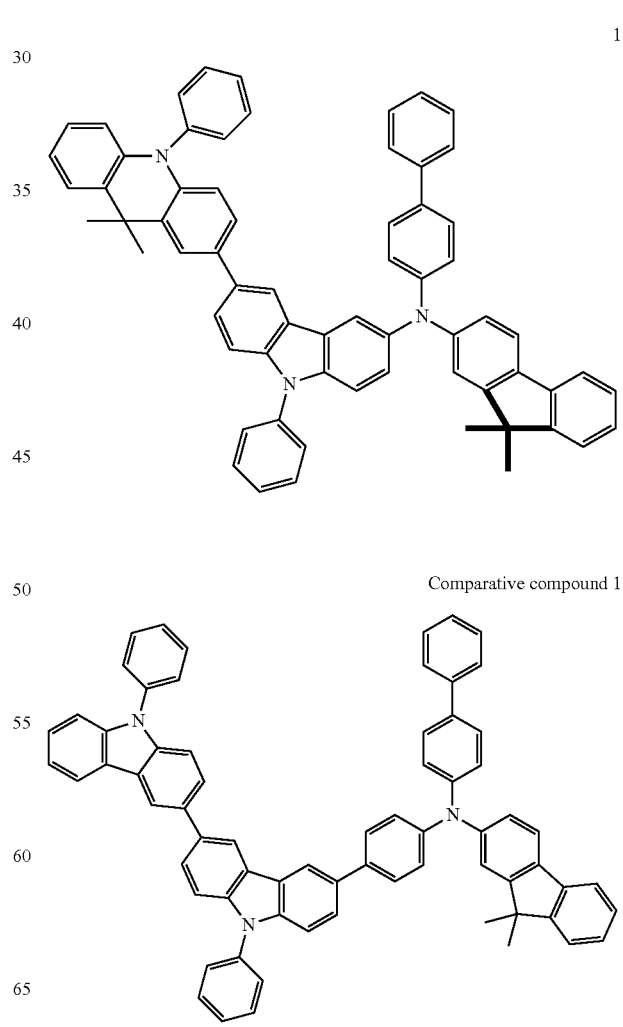

Comparative compound 2

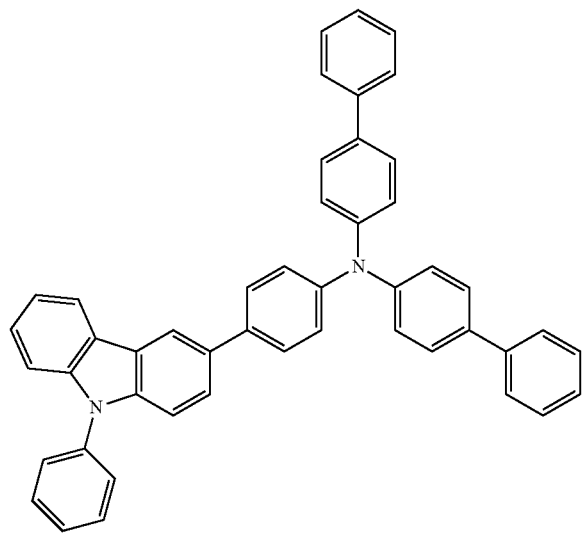

Comparative compound 3

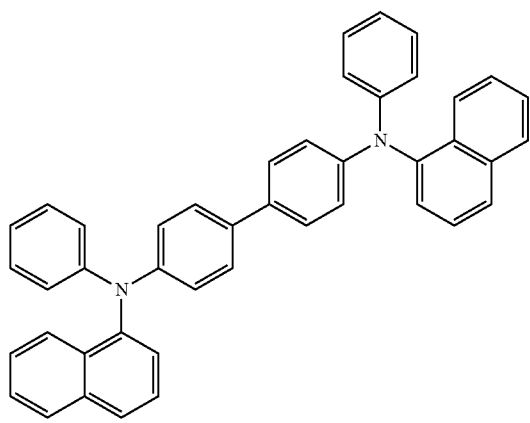

FIG. 1 illustrates a structure of an organic EL device used for measurement. Referring to FIG. 1, the organic EL device included a glass substrate 102, an anode 104 on the glass substrate 102 and formed of indium tin oxide (ITO), a hole injection layer 106 on the anode 104 and including 1-TNATA (4,4',4"-tris(N-(1-naphthyl)-N-phenylamino)triphenylamine, a hole transport layer 108 on the hole injection layer 106 and including one of the above-described Compound 1, Comparative compound 1, Comparative compound 2, orComparative compound 3, a light-emitting layer 110 on the hole transport layer 108 and formed of a host material including ADN (9,10-di(2-naphthyl)anthracene) and doped with tetra-t-butylperylene (TBP) to a concentration of 3%, an electron transport layer 112 on the light-emitting layer 110 and including Alq3, an electron injection layer 114 on the electron transport layer 112 and including LiF, and a cathode 116 on the electron injection layer 114 and formed of aluminum (Al). The anode 104 was 150 nm thick, the hole injection layer 106 was 60 nm thick, the hole transport layer 108 was 30 nm thick, the light-emitting layer 110 was 25 nm thick, the electron transport layer 112 was 25 nm thick, the electron injection layer 114 was 1 nm thick, and the cathode 116 was 100 nm thick.

While power was connected to the anode 104 and the cathode 116 to allow current to flow through the organic EL device 100 (in which Compound 1, Comparative compound 1, Comparative compound 2, or Comparative compound 3 was used as a material for the hole transport layer 108), the luminous efficiency of the organic EL device 100 was measured. The measured results are shown in Table 1, below. The luminous efficiency was measured at 10 mA/cm$^2$.

TABLE 1

| | Compound 1 | Comparative compound 1 | Comparative compound 2 | Comparative compound 3 |
|---|---|---|---|---|
| Voltage (V) | 7.3 | 7.4 | 7.5 | 8.1 |
| Luminous efficiency (cd/A) | 7.2 | 6.6 | 6.2 | 5.3 |

As may be seen in Table 1, compared to the organic EL devices that used Comparative compound 1, Comparative compound 2, and Comparative compound 3 as hole transport materials, the organic EL device that used Compound 1 (an amine derivative having an acridine group and a carbazole group according to an embodiment) exhibited improved luminous efficiency.

When the amine derivative having an acridine group and a carbazole group according to an embodiment is used as a material for the hole transport layer of an organic EL device, luminous efficiency of the organic EL device may be improved.

While the above embodiments show and describe that the amine derivative having an acridine group and a carbazole group according to an embodiment is used as an organic EL material of a passive type organic EL device, the embodiments are not limited thereto. For example, the amine derivative having the acridine group and the carbazole group may be used as an organic EL material of an active type organic EL device to thus improve the luminous efficiency of the active type organic EL device.

The organic EL device that uses or includes the amine derivative having the acridine group and the carbazole group according to an embodiment as a material for the hole transport layer may be employed in an organic EL display, a lighting apparatus, or the like.

By way of summation and review, holes and the electrons injected into the light-emitting layer may be recombined to generate excitons within the light-emitting layer. The organic EL device may emit light generated by radiation and non-activation of the excitons.

In application of the organic EL device to a display apparatus, high efficiency and long lifespan of the organic EL device are desirable. In order to achieve high efficiency and a long lifespan, normalization, stabilization and durability of the hole transport layer may be considered.

The embodiments may provide organic EL materials that improve luminous efficiency.

The embodiments may provide an organic EL device in which transportability of the hole transport layer may be improved.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence material represented by Formula 1, below:

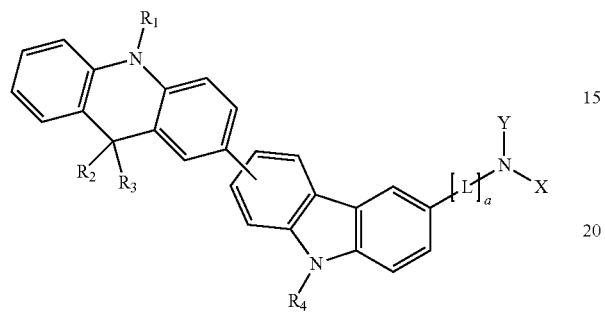

Formula 1 wherein:
X and Y are each independently an aryl group or a heteroaryl group having 6 to 18 carbon atoms,
L is an arylene group or a heteroarylene group having 6 to 18 carbon atoms,
$R_1$, $R_2$, $R_3$, and $R_4$ are each independently a hydrogen atom, a halogen atom, an aryl group or heteroaryl group having 6 to 18 carbon atoms, or an alkyl group having 1 to 12 carbon atoms, and
a is 0, 1, 2, or 3.

2. The organic electroluminescence material as claimed in claim 1, wherein X is a monovalent group represented by any one of groups (2), (3), (4), (5), (6), (7), (8), (9), or (10), below:

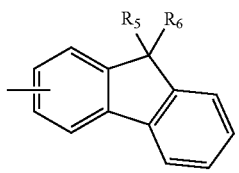

(2)

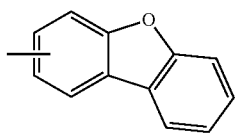

(3)

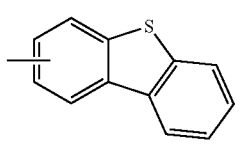

(4)

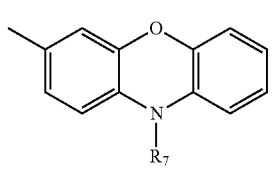

(5)

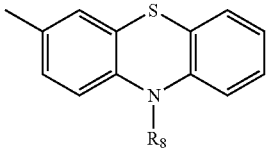

(6)

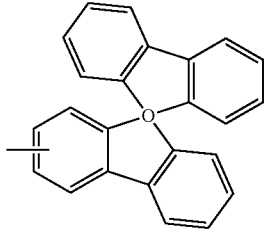

(7)

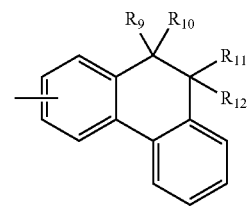

(8)

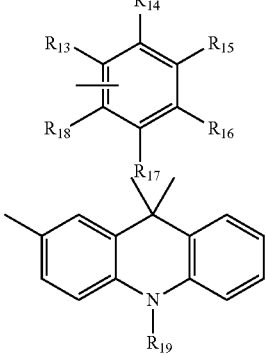

(9)

(10)

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{19}$ are each independently a hydrogen atom, a halogen atom, an aryl group or heteroaryl group having 6 to 18 carbon atoms, or an alkyl group having 1 to 12 carbon atoms.

3. An organic electroluminescence device, comprising an organic electroluminescence material represented by Formula 1, below:

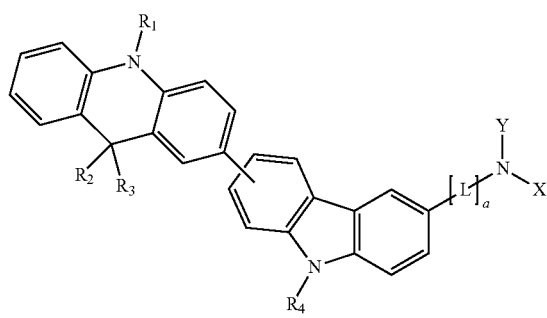

Formula 1 wherein:
X and Y are each independently an aryl group or a heteroaryl group having 6 to 18 carbon atoms, L is an arylene group or a heteroarylene group having 6 to 18 carbon atoms, $R_1$, $R_2$, $R_3$, and $R_4$ are each independently a hydrogen atom, a halogen atom, an aryl group or heteroaryl group having 6 to 18 carbon atoms, or an alkyl group having 1 to 12 carbon atoms, and a is 0, 1, 2, or 3.

4. The organic electroluminescence device as claimed in claim 3, wherein X is a monovalent group represented by any one of groups (2), (3), (4), (5), (6), (7), (8), (9), or (10), below:

(2)
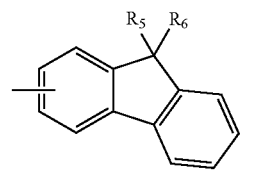

(3)
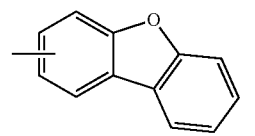

(4)
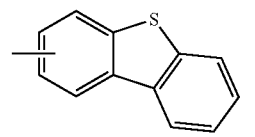

(5)
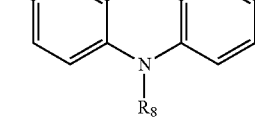

(6)
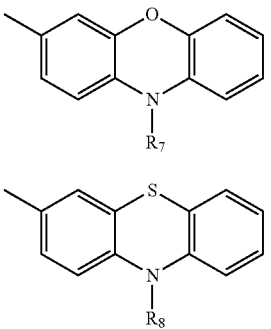

(7)
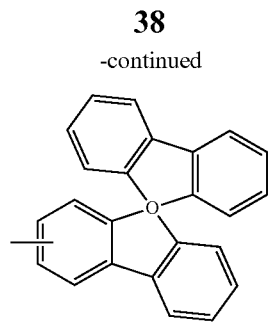

(8)
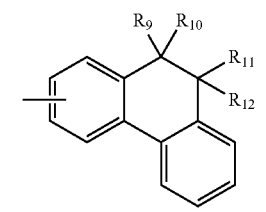

(9)
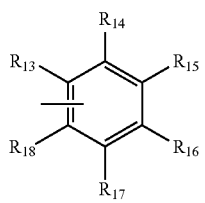

(10)
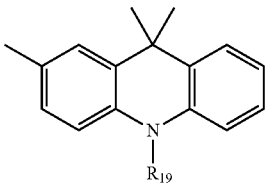

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{19}$ are each independently a hydrogen atom, a halogen atom, an aryl group or heteroaryl group having 6 to 18 carbon atoms, or an alkyl group having 1 to 12 carbon atoms.

5. An organic electroluminescence device, comprising an organic electroluminescence material represented by any one of compounds 1, 2, 3, 4, 5, 6, 7, 8, 9, 10, 11, 12, 13, 14, 15, 16, 17, 18, 19, 20, 21, 22, 23, and 24, below:

1
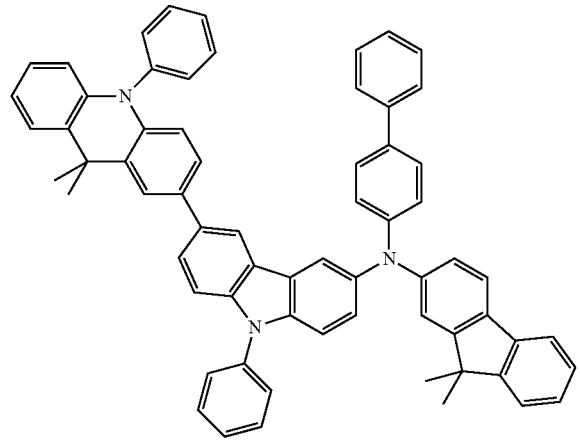

2
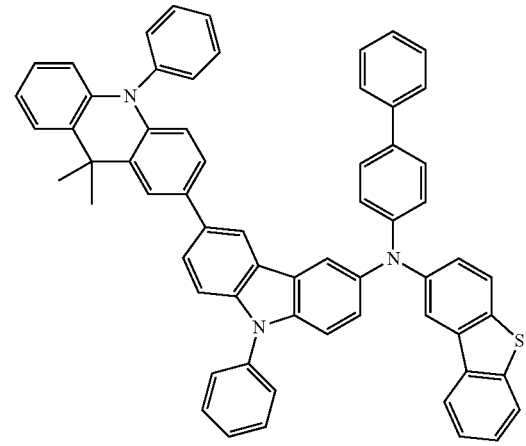

-continued
3
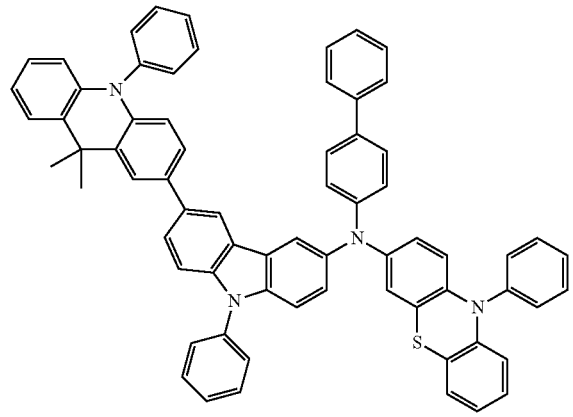
4
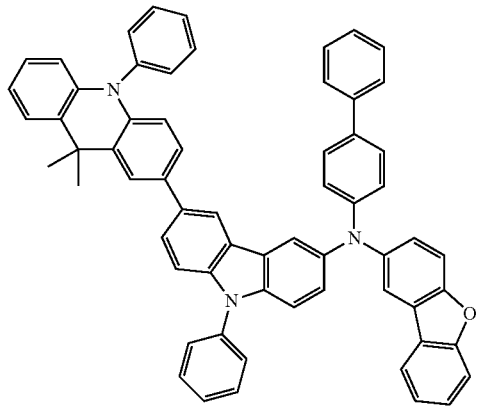
5
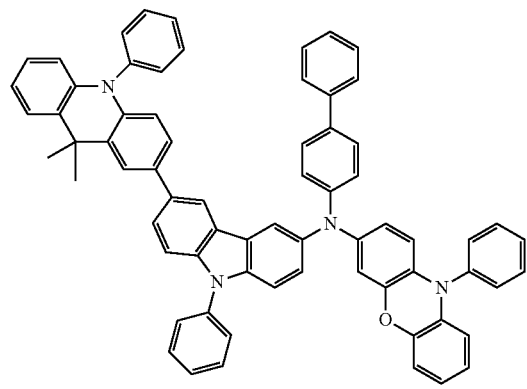
6
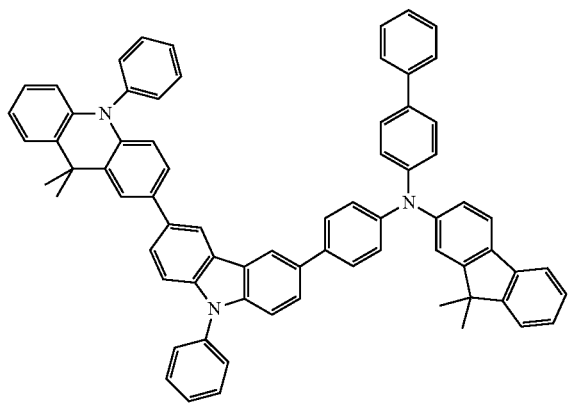
7
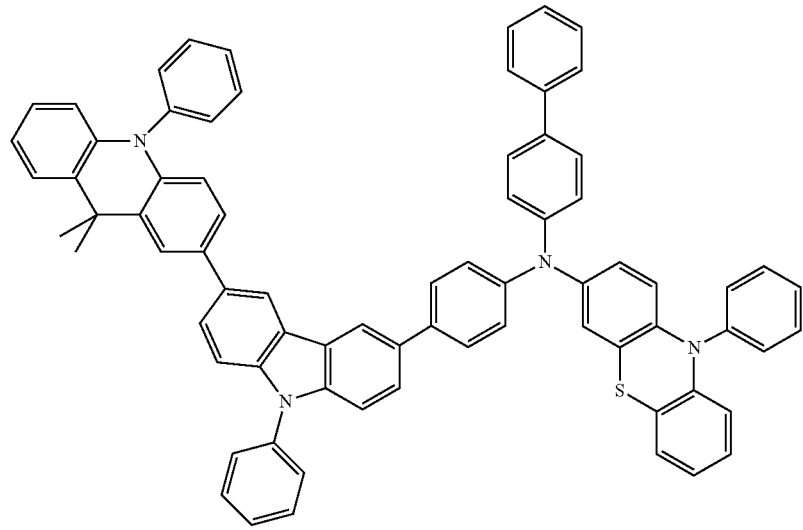

8
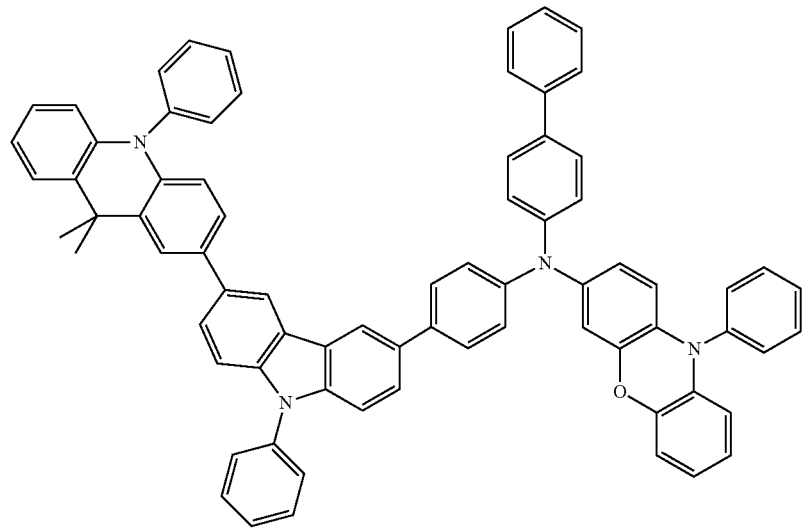
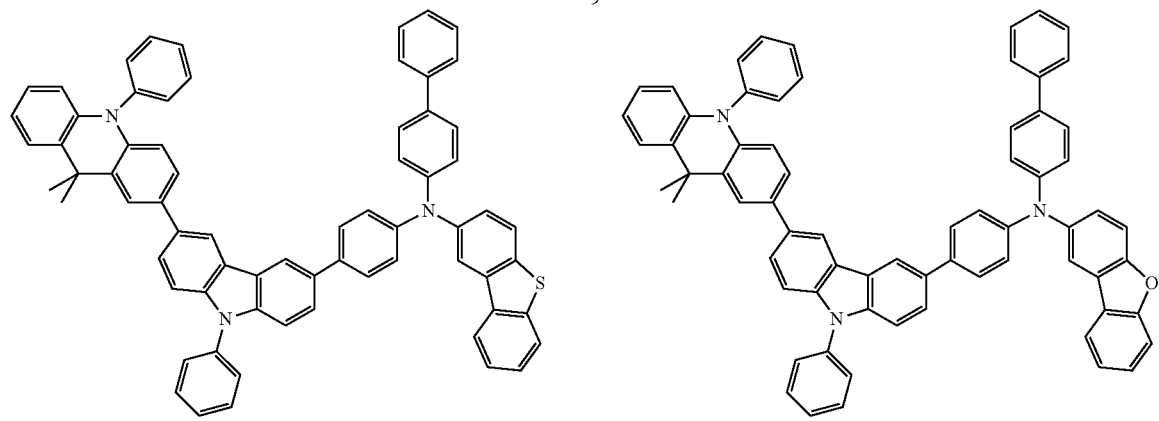
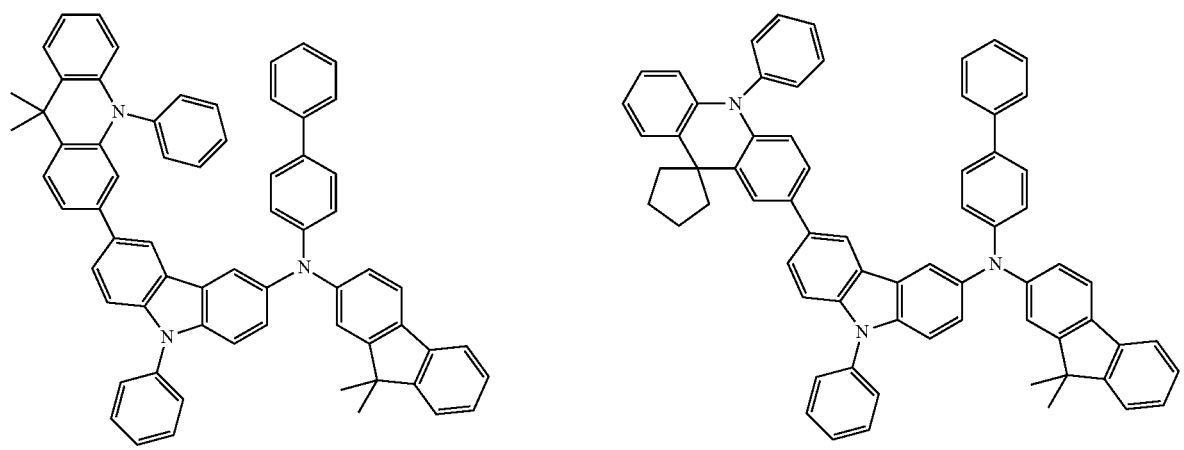

-continued
13
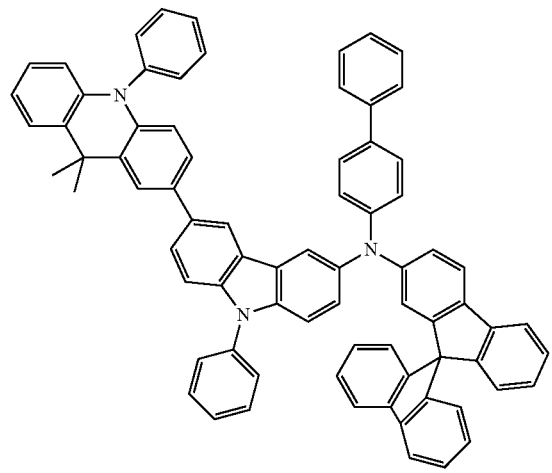
14
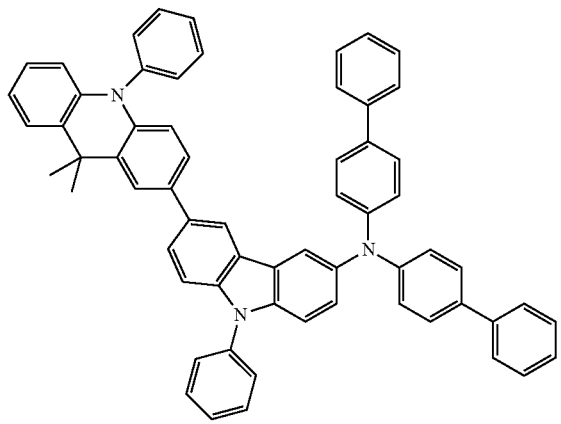
15
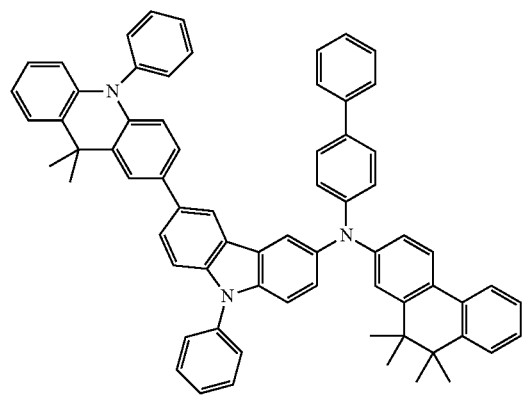
16
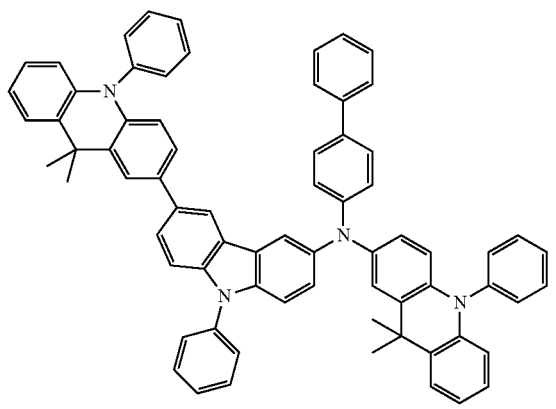
17
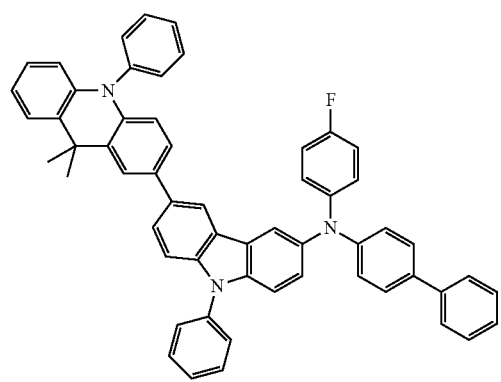
18
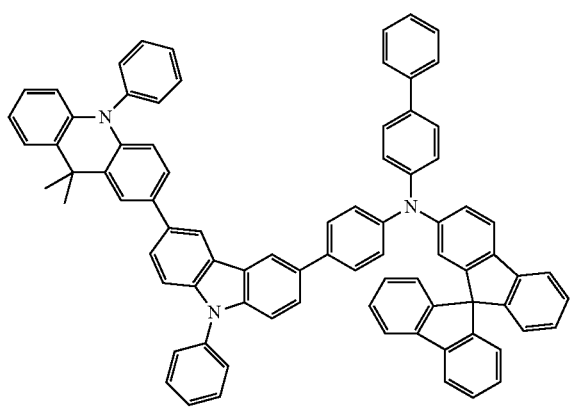

-continued
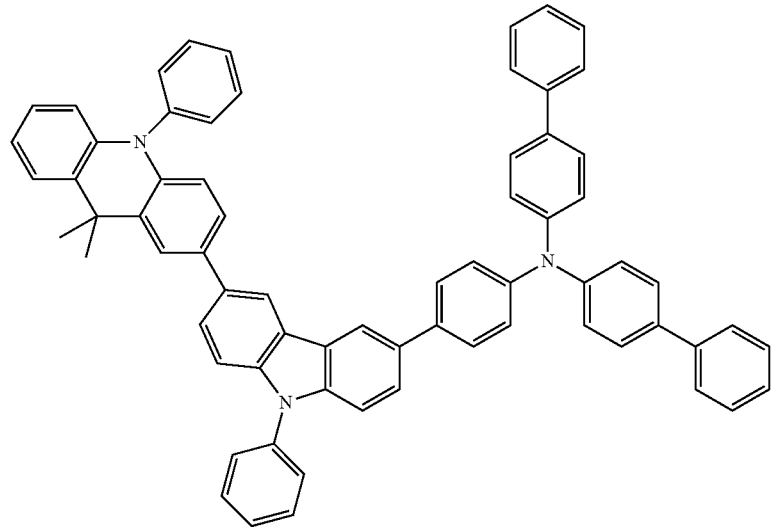
19
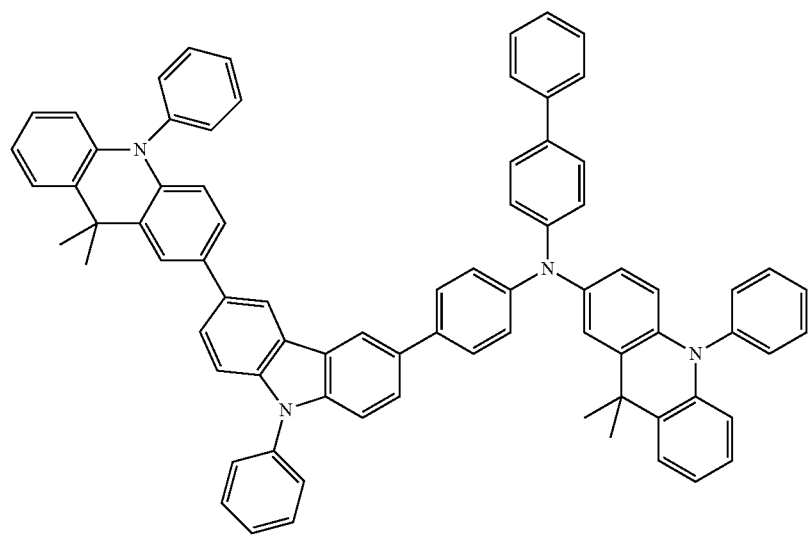
20
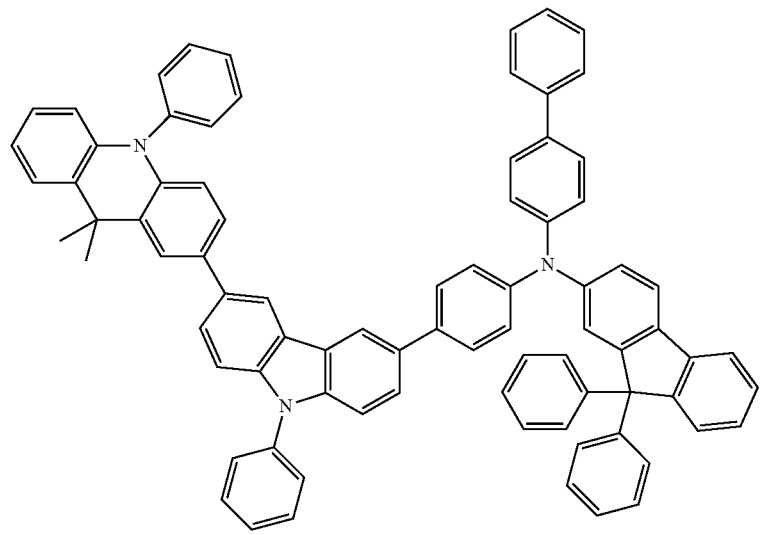
21

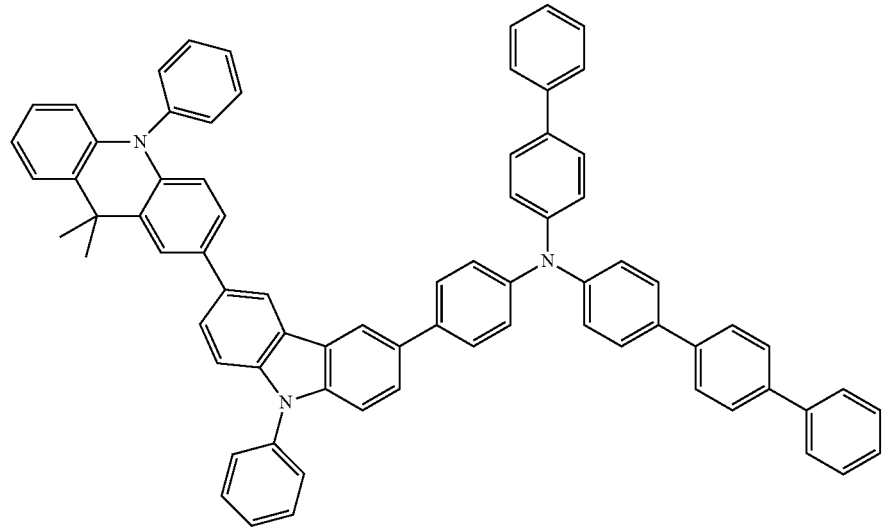
22
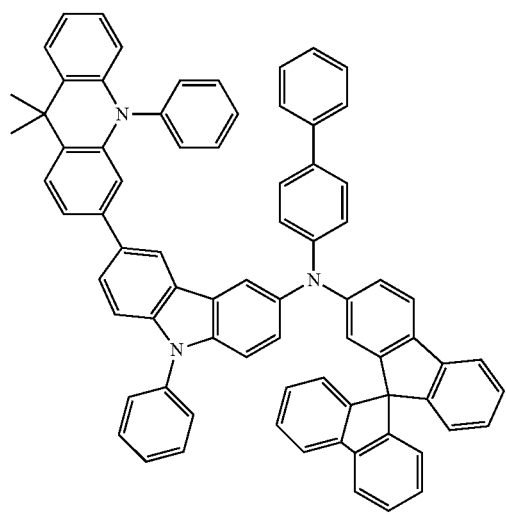
23
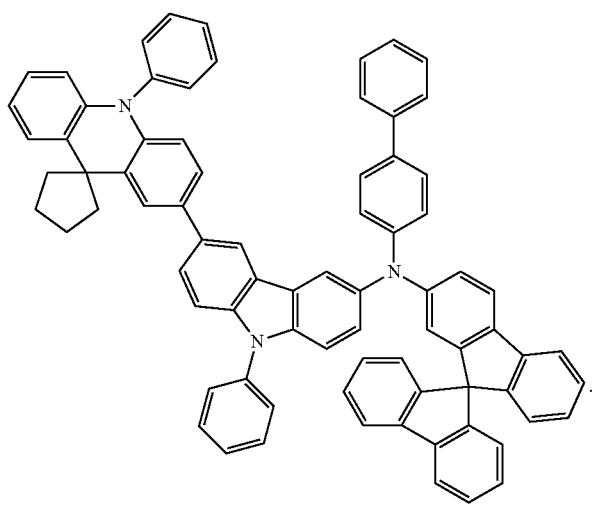
24
* * * * *